United States Patent [19]

Peltonen

[11] Patent Number: 4,768,518
[45] Date of Patent: Sep. 6, 1988

[54] PRESSURE CONTROL SYSTEM AND APPARATUS FOR THE CUFF OF AN AUTOMATIC NON-INVASIVE BLOOD PRESSURE METER

[75] Inventor: Pentti Peltonen, Helsinki, Finland

[73] Assignee: Instrumentarium Corp., Finland

[21] Appl. No.: 910,631

[22] Filed: Sep. 23, 1986

[30] Foreign Application Priority Data

Oct. 1, 1985 [FI] Finland ............................ 853781

[51] Int. Cl.$^4$ .............................................. A61B 5/02
[52] U.S. Cl. ................................... 128/677; 128/685; 137/513.3
[58] Field of Search .............. 128/672, 677–686, 128/327; 137/226, 513.3

[56] References Cited

U.S. PATENT DOCUMENTS

| | | |
|---|---|---|
| 3,550,582 | 12/1970 | Wilhelmson . |
| 3,552,385 | 1/1971 | Janssen . |
| 3,633,568 | 1/1972 | Hobel . |
| 3,929,129 | 12/1975 | Archambault ...................... 128/677 |
| 4,130,114 | 12/1978 | Peeler .................................. 128/677 |
| 4,204,545 | 5/1980 | Yamakoshi . |
| 4,206,764 | 6/1980 | Williams ............................. 128/677 |
| 4,501,280 | 2/1985 | Hood, Jr. ............................ 128/677 |
| 4,587,974 | 5/1986 | Link ................................ 128/677 X |
| 4,667,672 | 5/1987 | Romanowski ................. 128/686 X |

FOREIGN PATENT DOCUMENTS

| | | |
|---|---|---|
| 1194251 | 6/1970 | United Kingdom . |
| 1221331 | 2/1971 | United Kingdom . |
| 2087238 | 5/1982 | United Kingdom ................ 128/680 |

*Primary Examiner*—Kyle L. Howell
*Assistant Examiner*—Angela D. Sykes
*Attorney, Agent, or Firm*—Andrus, Sceales, Starke & Sawall

[57] ABSTRACT

The invention relates to a pressure control system and apparatus for the cuff of an automatic blood pressure meter. Pressure reduction is adapted to be effected by using at least two constrictions (3) having a constant constriction, the selection and combination of such constrictions being performed by digitally controlled magnetic valves (4). Such magnetic valves are controlled by a microprocessor (6) depending on a measuring value provided by a sensor (7) for measuring the cuff pressure transition rate so as to obtain a desired, approximately linear rate of pressure reduction. The constrictors (3) comprise thin flexible tubes. The system is capable of compensating automatically for the changes caused in the desired volume air flow by the cuff size and tightness, variations in the circumference of a person's arm, the heartbeat density and pressure range.

12 Claims, 1 Drawing Sheet

PRESSURE CONTROL SYSTEM AND APPARATUS FOR THE CUFF OF AN AUTOMATIC NON-INVASIVE BLOOD PRESSURE METER

BACKGROUND OF THE INVENTION

In conventional blood pressure measurement by the application of auscultation technique, the measuring is effected by using a manually operated air pump for pumping a pressure higher than systolic blood pressure into a blood pressure cuff which is usually fastened around the arm. Thereafter, the cuff pressure is reduced uniformly while listening to so-called Korotkoff sounds by means of a stethoscope. The cuff pressures corresponding to certain transition points in these sounds indicate systolic and diastolic blood pressures.

In manual blood pressure measuring, the measurer can arbitrarily control the rate of pressure reduction in such a manner that all factors having effect on measuring can be considered for setting thereby the rate of pressure reduction appropriate at a given moment. The pressure reduction can also be completely stopped and it is also possible to increase pressure with a hand pump during the measuring process.

An automatic blood pressure meter must be capable of controlling the rate of pressure reduction independently. This can be effected by measuring the cuff pressure and its reduction rate by means of a pressure transducer and by adjusting in accordance therewith a needle valve e.g. by means of a stepping motor. Since the same device must be capable of measuring with cuffs of varying sizes over a wide pressure range, a valve to be used in pressure reduction must be capable of operating over a wide range of volume flow. In order to maintain a constant rate of pressure reduction, it is necessary that a valve used for pressure reduction during the measuring be ajustable. This leads to sophisticated mechanical precision designs, whose industrial manufacturing is complicated and which are extremely sensitive to malfunctions caused by dust.

BRIEF DESCRIPTION OF THE PRESENT INVENTION

An object of the invention is to provide a system, wherein a pressure control system for the cuff of an automatic blood pressure meter can be set up by using simple flexible constriction tubes and magnetic valves. The system is controlled by a microprocessor which facilitates the introduction of several additional features for improved control. The characterizing features of the invention are set out in the annexed claims.

BRIEF DESCRIPTION OF THE DRAWING

A system of the invention and a general block diagram of the apparatus are illustrated in FIG. 1.

The pressure control achieved by the system and apparatus of the present invention is illustrated in FIG. 2.

DETAILED DESCRIPTION OF THE PREFERRED EMBODIMENT

Figure 1:
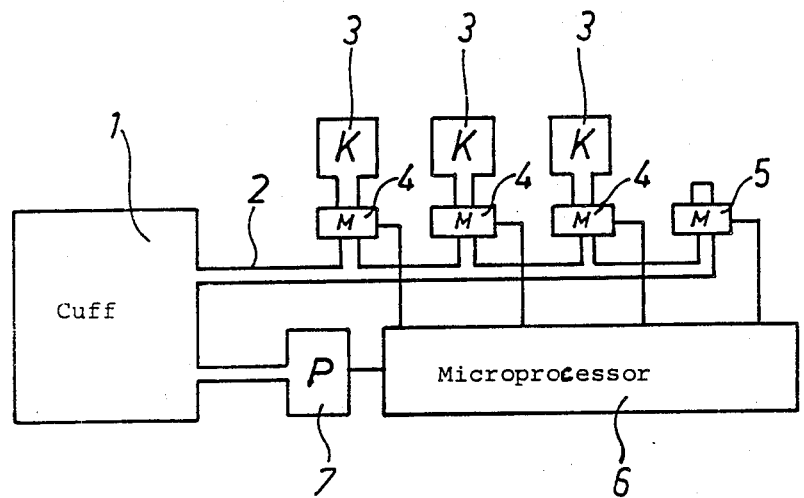

A pressure reduction line 2 for a cuff 1 is provided with three parallel constriction elements 3 having a constant constriction. In series with each constriction element 3 are magnetic valves 4 which are controled by a microprocessor 6 depending on the information provided by a pressure reduction measuring element 7. A magnetic valve 5 can be used to release pressure from cuff 1.

Figure 2:
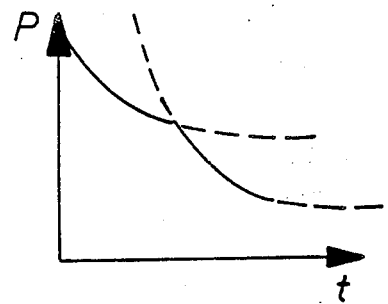

Operation of the system is such that microprocessor 6 receives information about the rate of pressure reduction by way of said element 7 measuring the rate of pressure reduction. On the basis of this information, said microprocessor 6 operates magnetic valves 4 to switch on a constriction element 3 appropriate for obtaining a proper rate of pressure reduction. One fixed constriction element 3 is capable of producing a rate of pressure reduction roughly proportional to the pressure, which rate, as such, can only be used in a very narrow pressure range. In order to achieve an approximately linear rate of pressure reduction in a given pressure range, one constriction element 3 should be used at a higher pressure and another at a lower pressure. Obtained this way is an approximately linear pressure reduction as shown in FIG. 2.

Each cuff size requires in principle two constriction elements for itself. By selecting the constrictions properly, the constrictions required by different cuff sizes and pressure ranges can be combined in a manner that the adjustment of the pressure reduction rate of three standard cuffs can be effected e.g. by means of three constriction elements over the entire measuring range required. For further improving the adjustment or control, it is possible to use combinations of different constriction elements. Thus, for example, six different flow rates can be achieved by means of three constrictions.

The operating range of this system can be expanded indefinitely by increasing the number of magnetic valves and constriction elements. The same way, by increasing the number of elements, it is possible to improve the linearity of adjustment indefinitely.

A processor can effect the adjustment of a pressure reduction rate within certain limits by bringing upwards or downwards the pressure value at which the constriction is changed. This way, by using a few fixed constrictions, it is possible to set up a system that has rather good control characteristics.

Constriction elements 3 are made of thin flexible tube. An advantage offered by this solution over generally used capillary constrictions is that they are considerably more insensitive to dust and they are very stable.

The adjustment of a flexible tube constriction is easy compared with other solutions. The adjustment of constriction can be effected by simply cutting off the flexible tube.

The adjustment effected by means of a microprocessor can bring about some additional functions that are useful for the measuring and could not be achieved by means of an independently operating pressure control system.

Various cuff sizes can be identified automatically on the basis of the constriction required thereby.

Tightness of a cuff around the arm may vary considerably. A result of this is that the amount of air present in a cuff varies within wide limits. A microprocessor can compensate for the change in the rate of pressure reduction caused by unequal amounts of air in a cuff by bringing the constriction transition pressure up or down for obtaining the desired rate of pressure reduction.

Variations in the circumference of a person's arm have an effect on the results and so do variations in the cuff tightness. This can also be compensated for the same way as above.

Instead of a certain fixed rate of pressure reduction, the control rating applied can be a certain pressure drop per a single heartbeat or it is possible to use a combination of these two.

The operator can adjust or control the pressure reduction rating within certain limits. This gives the operator a possibility of making a suitable compromise regarding accuracy of the result and speed of measuring.

I claim:

1. A pressure control system for reducing the pressure in a fluid pressurizable cuff of an automatic sphygmomanometer at a substantially constant rate, said system comprising:
   a pressure reduction line (2) coupled to the cuff (1);
   at least a pair of constriction elements (3) coupled to said pressure reduction line and forming constricting paths for discharging fluid from the cuff to reduce the pressure therein, each of said elements possessing a constant magnitude fluid flow constriction property;
   an on-off valve means (4) operatively associated with each of said constriction elements, said valve means closing each of said constriction elements and opening each of said constriction elements to provide the constricted discharge path;
   means (7) for sensing the pressure in the cuff; and
   control means (6) coupled to said pressure sensing means and to said valve means, said control means sequentially operating individual valve means or combinations thereof responsive to the pressure sensed in the cuff by said pressure sensing means to obtain a fluid discharge through said constriction elements providing a pressure reduction in the cuff that is approximately linear with respect to time.

2. The pressure control system according to claim 1 wherein said constriction elements comprise thin, flexible tubes.

3. The pressure control system according to claim 2 wherein said tubes present differing constant magnitude fluid flow constriction properties with respect to each other.

4. The pressure control system according to claim 3 wherein the constriction element tubes are of differing lengths.

5. The pressure control system according to claim 1 wherein said constriction elements present differing, constant magnitude fluid flow constriction properties with respect to each other.

6. The pressure control system according to claim 1 including three constriction elements coupled to said pressure reduction line.

7. The pressure control system according to claim 1 wherein said valve means comprise magnetic valves.

8. The pressure control system according to claim 1 wherein said control means comprises a microprocessor.

9. The pressure control system according to claim 1 wherein said control means comprises a digital microprocessor means and wherein said valve means comprise digitally controlled magnetic valves.

10. The pressure control system according to claim 1 wherein said control means is further defined as operating said valve means reponsive to the occurrence of preselected pressure levels in the cuff.

11. The pressure control system according to claim 10 wherein said control means is further defined as being adjustable to operate said valve means at different preselected pressure levels.

12. The pressure control system according to claim 1 including a pressure dump valve (5) coupled to said pressure reduction line.

* * * * *